(12) United States Patent
Nakae et al.

(10) Patent No.: US 6,892,141 B1
(45) Date of Patent: May 10, 2005

(54) PRIMER DESIGN SYSTEM

(75) Inventors: Hiroki Nakae, Fujisawa (JP); Sigeo Ihara, Tokorozawa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/527,440

(22) Filed: Mar. 17, 2000

(51) Int. Cl.[7] .......................... C12P 19/34; C07H 21/02; C07H 21/04; G06F 19/00
(52) U.S. Cl. ...................... 702/20; 435/91.1; 435/91.2; 435/91.21; 536/23.1; 536/24.3
(58) Field of Search ............... 435/91.1, 91.2, 435/91.21; 536/23.1, 24.3, 24.31–24.33, 24.8, 29.32; 935/77, 78, 88, 87, 1–9, 10, 16, 17; 702/20

(56) References Cited

U.S. PATENT DOCUMENTS

| | | | | |
|---|---|---|---|---|
| 5,176,995 | A | * | 1/1993 | Sninsky et al. ................. 435/6 |
| 6,007,231 | A | * | 12/1999 | Vijg et al. |
| 6,083,763 | A | * | 7/2000 | Balch .......................... 436/518 |
| 6,251,588 | B1 | * | 6/2001 | Shannon et al. ................ 435/6 |

FOREIGN PATENT DOCUMENTS

WO   WO 98/06872   *   2/1998

OTHER PUBLICATIONS

Harris Genome Research (1997) vol. 7, No. 7: pp.754–762.*
Xu, G. et al. Genomics vol. 47, pp. 171–179 (1998).*
Lowe et al. A computer program for selection of oligonucleotide primers for polymerase chain reactions. Nucleics Acids Research, vol. 18 No. 7 pp. 1757–1761.*
Kariko, Identification of conserved sequences for PCR primer design by multiple alignments of dot matrix plots. BioTechniques, vol. 18(6), pp. 1048–1049 (1995).*

Junko Inoue, Toshiyuki Saito, Nobuaki Hayashida, Nobuyuki Miyajima, "Selection of primers in PCR", Feb. 5, 1995, pp. 18–24 (in Japanese, with relevant contents translated into English).

Lashkari et al., "Yeast microarrays for genome wide parallel genetic and gene expression analysis," Proc. Natl. Acad. Sci. USA 94 (Sep. 1997), pp. 13057–13062.

Hillier, Green; OSP: a computer program for choosing PCR and DNA sequencing primers; PCR Methods Appl., PP 124–8, Nov. 1991.

Hosokawa Mitsuhashi; Novel computerized method for designing nucleotide sequence used for DNA probes and PCR primers; Nippon Rinsho, PP530–41, Feb. 1994.

Lincoln, Stephen et al.; PRIMER: A Computer Program for Automatically Selecting PCR Primers, PRIMER, Whitehead Inst. Of Biomedical Research, Version 0.5, May 1991.

Becker, A. et al.; Primer Design—a new program to choose PCR primers and oligonucleotide probes; Medizinische Genetik 7(2): (1995) A–158.

Dieffenbach C.W.; General Concepts for PCR Primer Design; PCR Methods and Applications, PP 530–537, Manual Supplement, 1993.

* cited by examiner

*Primary Examiner*—Marjorie Moran
*Assistant Examiner*—Lori A. Clow
(74) *Attorney, Agent, or Firm*—Reed Smith LLP; Stanley P. Fisher, Esq.; Juan Carlos A. Marquez, Esq.

(57) ABSTRACT

A primer design system in which DNA nucleotide sequences are obtained from a database comprising a plurality of different DNA nucleotide sequences, and the nucleotide sequences of primers capable of hybridizing specifically to the DNA thus obtained are determined. A plurality of primers capable of hybridizing specifically to mutually different DNAs can be efficiently designed.

10 Claims, 8 Drawing Sheets

EXON 1

```
  1 acaacagaacaacagggagccctatcttcagaactgccaagcacatcaccttcatcagtt
 61 gctgccatttcatcgagatcagtaatacacaaaccatttactcagtcccggatacctcca
121 gatttgcccatgcatccggcaccaaggcacataacggaggaagaactttctgtgctggaa
181 agttgtttacatcgctggaggacagaaatagaaatgacaccagagg
```

| Tm | GC CONTENT | SEQUENCE |
|---|---|---|
| Tm=60 | 50.0% | acaacagaacaacagggaagc 5' |
| Tm=58 | 45.0% | aagataaagacaggaggtcg 3' |

EXON 2

```
  1 acaagcagcaggagacccagaatatctagagcagccatcaagaagtgatttctcaaagca
 61 cttgaaagaagaaactattcaaataattaccaaggcatcacatgagcatgaagataaaag
121 tcctgaaacagttttgcagtcgg
```

| Tm | GC CONTENT | SEQUENCE |
|---|---|---|
| Tm=62 | 55.0% | aagcagcaggagacccagaa 5' |
| Tm=58 | 45.0% | ggctgacgttttgacaaagt 3' |

EXON 3

```
  1 aacctgaaaatactacaagccaaccactttctaatcagcgagttgtagaggtggcgatcc
 61 ctcatgtagggaaatttatgattgaatcaaaggagggggggtatgatgacgagg
```

| Tm | GC CONTENT | SEQUENCE |
|---|---|---|
| Tm=58 | 45.0% | actacaagccaaccactttc 5' |
| Tm=62 | 55.0% | agtagtatgggggggaggaa 3' |

EXON 4

```
  1 tccttaatttaaaaaggaaacaaaaacctattctttttttttttcctgcattgcattaaga
 61 aattaaatgagcaagccgcagaactcttcgaatctggagaggatcgagaagtaaacaatg
121 gtttgattatcatgaatgagtttattgtcccattttgccattattactggtggatgaaa
181 tggaagaaaaggatatactagctgtagaagatatgagaaatcgatggtgttcctaccttg
241 gtcaagaaatggaacg
```

| Tm | GC CONTENT | SEQUENCE |
|---|---|---|
| Tm=58 | 45.0% | ataaatgagcaagccgcag 5' |
| Tm=58 | 45.0% | gcaaggtaaagaactggttc 3' |

PRIMER DESIGN SYSTEM

BACKGROUND OF THE INVENTION

1. Field of the Invention

The present invention relates to a technique of DNA analysis, and more particularly to a primer design system, a method for designing primers, a storage medium on which is recorded a program for allowing a computer to function as a primer design system, a storage medium on which is recorded data which are necessary during DNA analysis, plates containing primers which are necessary during DNA analysis, a DNA analysis kit comprising a storage medium and primers which are necessary during DNA analysis, and a method for analyzing DNA.

2. Description of the Related Art

In the 1990's, the human genome project has flourished, leading to an increasingly clearer understanding of the genome sequences for *E. coli*, yeasts, nematodes, rice, *Arabidopsis thaliana*, mice, rats, humans, and the like. This has been accompanied by a veritable explosion of highly efficient methods for the analysis of nucleotide sequences as well as the development of techniques such as the computerization of sequence analyses and higher throughput in techniques for the analysis of nucleotide sequences of the gene, YAC and BAC libraries, and chromosome markers.

Figure 1:
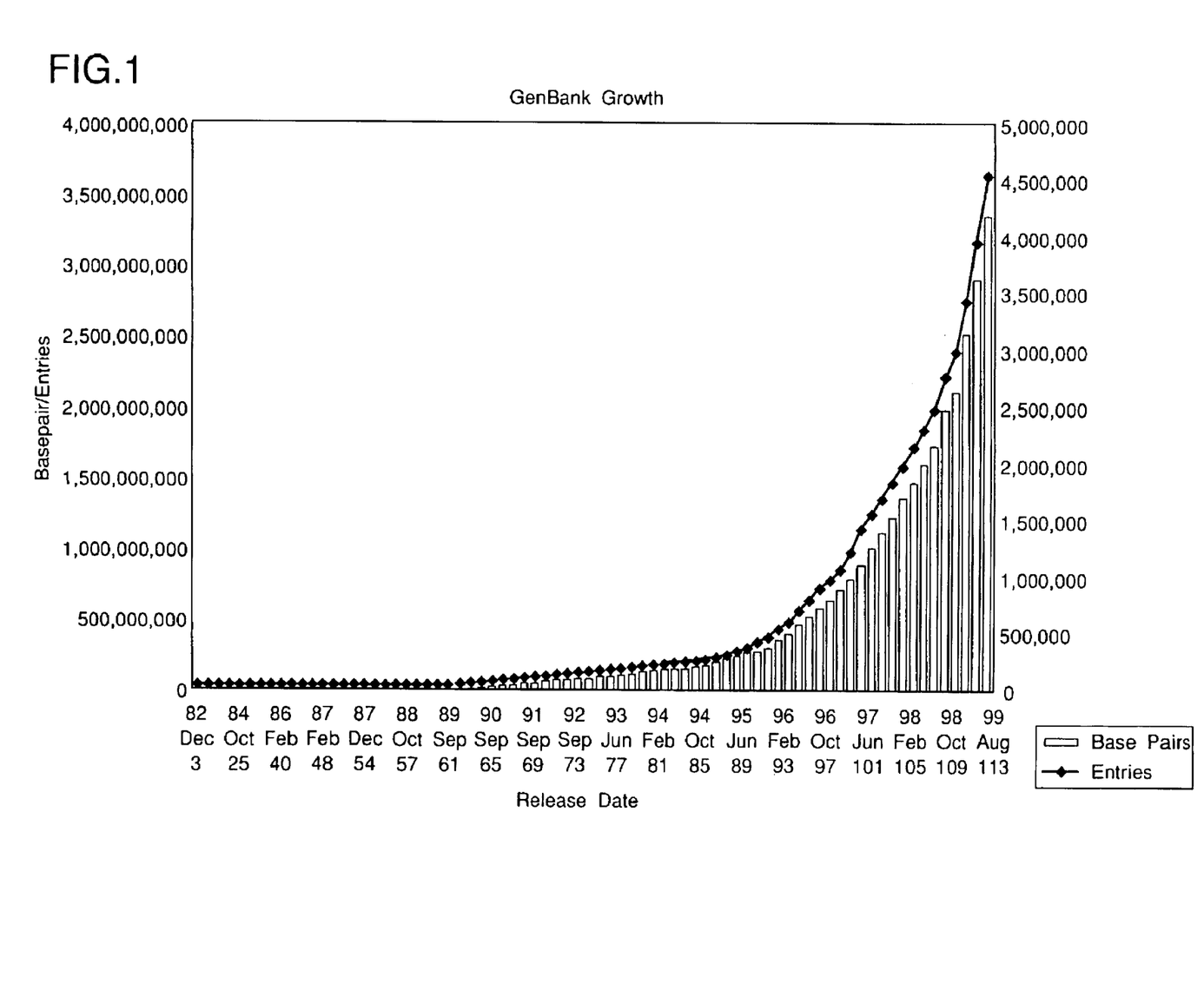
FIG. 1 illustrates changes in the number of nucleotide sequences registered at GenBank.

The recent progress of the genome project and the development of sequence analyzing techniques have resulted in the continuing accumulation of massive gene-related databases (see FIG. 1), making bioinformatics increasingly necessary in the data processing of such massive amounts of gene-related data. Bioinformatics is an expression created from biology and informatics (the science of information), meaning research combining life sciences and information sciences, that is, the comprehensive science of handling biological data in its entirety with the intention of making broader use not only of genome data but of biological data, from genes to protein structure or function. At present, however, bioinformatics is not being adequately used in industry-based genetic functional analysis.

Genomic DNA includes both intron and exon regions. Of these, exons encode proteins, making the analysis of exons extremely important in genetic analysis. However, it is extremely difficult to specify exons that are compatible with the actual purpose of research, and conventional genetic analysis has involved selecting exons compatible with the purpose of research merely through trial and error.

Figure 7:
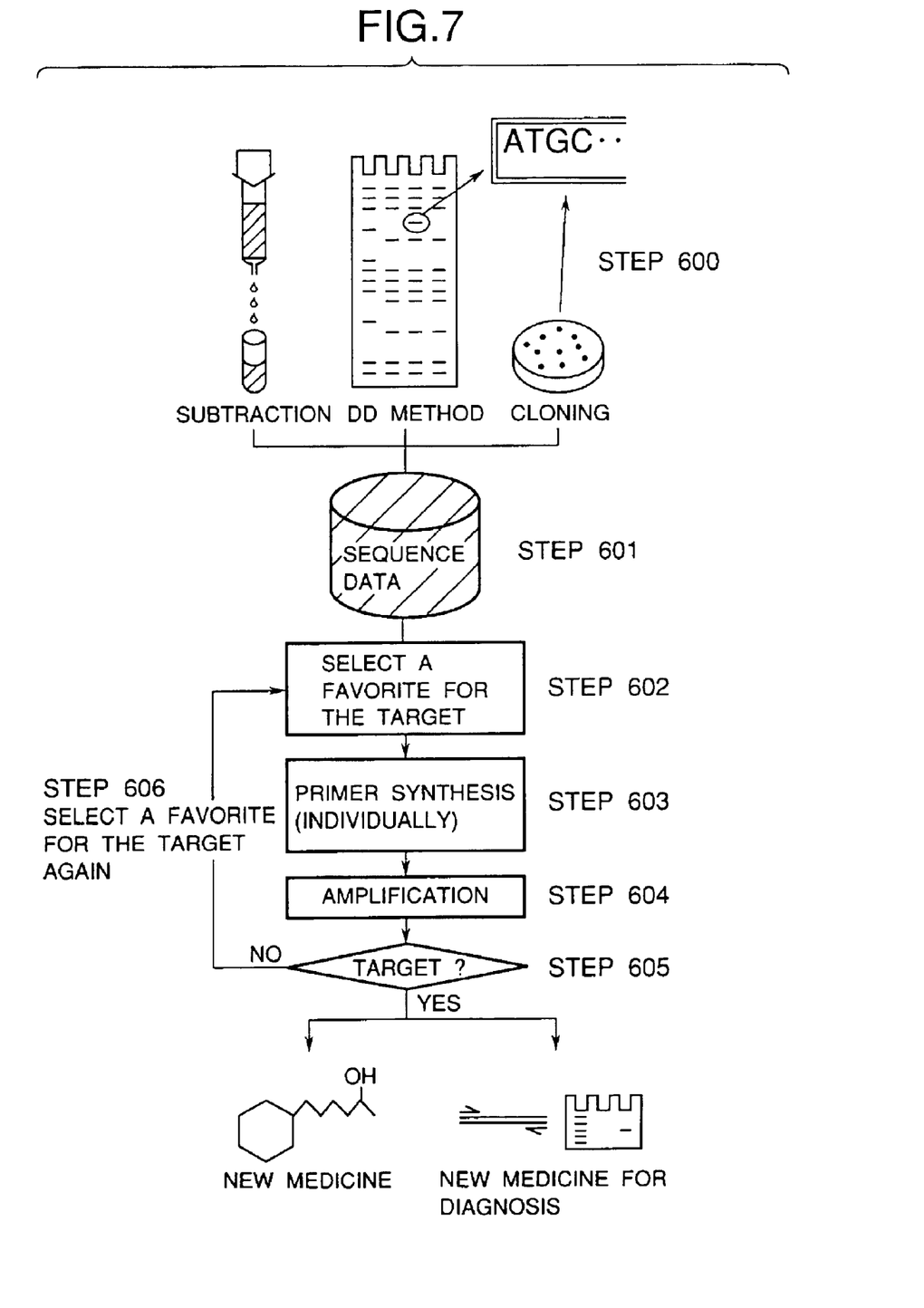
FIG. 7 illustrates a conventional method of DNA analysis.

FIG. 7 depicts the course of conventional genetic analysis. Conventionally, the individual genes or proteins of interest are generally identified (step 600) by subtraction or DD based cloning of gene, nucleotide sequences or protein amino acid sequences, and then checked what type of functions they have. That is, exons which are considered compatible with the purpose of research are selected beforehand (step 602) from the identified nucleotide sequences to design corresponding primers (step 603). The primers are then used in PCR (polymerase chain reaction) to amplify the target exons (step 604) for analysis of the exons (step 605). PCR is a method in which primers are designed for both ends of the region that is to be amplified, and genes are amplified logarithmically by temperature cycles using a heat resistant DNA enzyme such as Taq DNA polymerase. Primers are oligonucleotides having an —OH at the 3' end necessary to initiate DNA synthesis.

When the exons selected by the analysis in step 605 prove to be incompatible with the purpose of the research in such conventional genetic analysis, the process (step 606) must be repeated from the exon selection in step 602, making it extremely important to ensure the reliable selection of exons compatible with the purpose of research. During the analysis of differences in gene levels occurring between normal individuals and patients afflicted with a certain disease (such as cancer), for example, exons which are the target of research will be the exons leading to the disease, but it is extremely difficult to determine which exons are the exons in question, and there has been no other way to analyze candidate exons other than by the trial and error described above in order to determine such exons.

SUMMARY OF THE INVENTION

The present invention is intended to provide a method for more efficiently designing primers for various genes of interest, which has been an inefficient undertaking in the past because of the extreme difficulty involved in specifying desired exons as described above.

More specifically, an object of the present invention is to provide a high-throughput method for genetic functional analysis which is completely different from conventional methods, by making use of "Bioinformatics" in genetic functional analysis, comprising nothing more than the use of various conventional databases, primer designing programs, primer detection programs, and the like as needed, separately.

Figure 8:
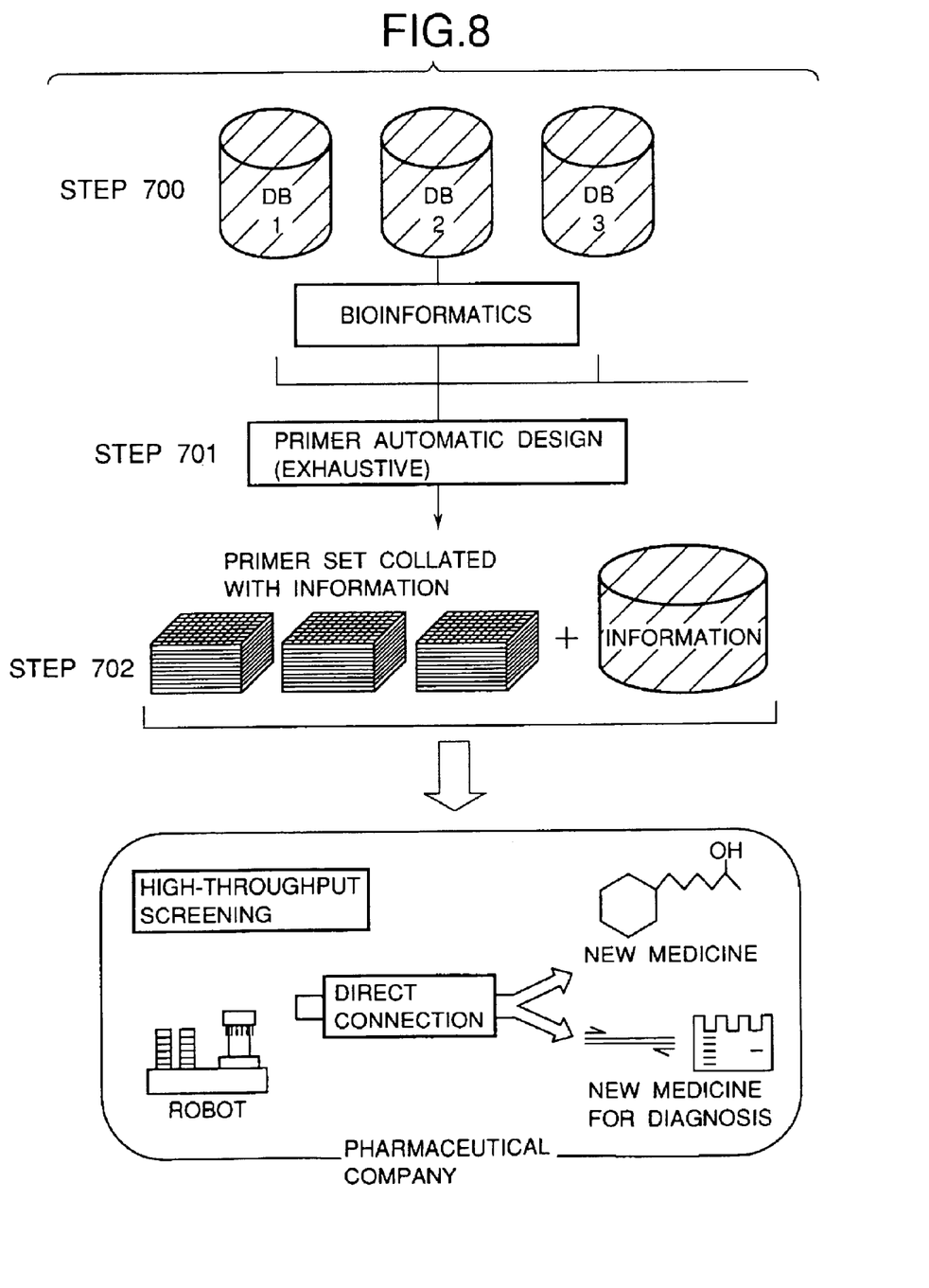
FIG. 8 illustrates the method of DNA analysis in the present invention.

To achieve the aforementioned objective, we devised a scheme completely the opposite of conventional methods of genetic analysis. The method of analysis in the present invention is depicted in FIG. 8. That is, in conventional methods, genetic analysis proceeds by a scheme in which the exon which is the target of research is first determined, and primers corresponding to the exon are then designed. In contrast to this, the inventors have devised a scheme in which a plurality of primers are first designed (step 701) for mutually different exons by means of bioinformatics from nucleotide sequence data compiled in public databases or the like (step 700), and DNA fragments which have been amplified by PCR using these primers are then analyzed. This scheme determines which exons are amplified by which primers beforehand (step 702) to make it easier to analyze DNA fragments amplified by PCR, resulting in more efficient analysis. For example, during the analysis of differences in gene levels occurring between normal individuals and patients afflicted with a certain disease (such as cancer), genomic DNAs extracted from the cells of various individuals are used as templates to carry out PCR using a plurality of primers for mutually different exons, and exons which are believed to be related to the disease can be determined based on types of primers having differences in nucleotide sequences and the length or presence/absence of amplified fragments. Thus, in the method of genetic analysis devised by the inventors, PCR is carried out using primers for mutually different exons, and exons compatible with the purpose of research are then determined and analyzed.

In this type of genetic analysis, it is necessary to prepare primers for as many exons as possible. Massive amounts of data have been compiled at present for genomic DNA nucleotide sequences and cDNA nucleotide sequences (see FIG. 1). We have constructed a primer design system in which a computer can be used to process data on DNA nucleotide sequences obtained from databases including a plurality of different DNA nucleotide sequences, so as to design a plurality of primers for mutually different DNAs, and we have also discovered that genetic analysis can be managed more efficiently by correlating the designed primer data and the genetic data of the DNA fragments amplified by PCR using such primers.

The present invention was perfected based on the above findings.

That is, the present invention comprises the following inventions:

(1) a primer design system, comprising: a receiver for obtaining data on a plurality of DNA nucleotide sequences from a first database having data on a plurality of different DNA nucleotide sequences; and a control unit for controlling the system, the aforementioned control unit controlling: extracting means for extracting partial sequences meeting certain base length extraction conditions from the plurality of DNA nucleotide sequences, the data for which were obtained by the aforementioned receiver; detecting means for detecting certain conditions related to the positions of the aforementioned partial sequences, and conditions of their absence in DNA sequences other than the aforementioned DNA nucleotide sequences; first selecting means for selecting partial sequences meeting the aforementioned conditions from the aforementioned partial sequences based on the results of the aforementioned detecting means; and determining means for determining the nucleotide sequence of primers capable of specifically hybridizing to the aforementioned plurality of DNA nucleotide sequences based on the results of the aforementioned first selecting means;

(2) a primer design system according to (1) above, the aforementioned control unit further controls second selecting means for selecting DNA nucleotide sequences meeting certain selection conditions from the partial sequences extracted by the aforementioned extracting means;

(3) a primer design system according to (2) above, the aforementioned selection conditions being related to GC content and/or Tm;

(4) a primer design system according to out of from (1) to (3) above, the aforementioned control unit further controls limiting means for limiting the plurality of DNA nucleotide sequences, the data for which were obtained by the aforementioned receiver, to a base length longer than the aforementioned prescribed base length, to be output to the aforementioned extracting means;

(5) a primer design system according to out of from (1) to (3) above, the aforementioned control unit further controls third selecting means for selecting DNA nucleotide sequences meeting selection conditions related to GC content and/or Tm based on the plurality of DNA nucleotide sequences, the data for which were obtained by the aforementioned receiver;

(6) a primer design system according to out of from (1) to (3) above, further comprising a second database including data for a plurality of different DNA nucleotide sequences, the aforementioned second database comprising at least one of either data on cDNA nucleotide sequences included in the aforementioned first database, or data on the exon nucleotide sequences predicted on the basis of genomic DNA nucleotide sequences included in the aforementioned first database, wherein the aforementioned extracting means targets the aforementioned nucleotide sequences included in the aforementioned second database for extraction;

(7) a storage medium having recorded thereon a program executable at the control unit in a computer having the aforementioned control unit and memory with data on a plurality of different DNA nucleotide sequences, the aforementioned program comprising instruction for reading data on a plurality of DNA nucleotide sequences in the afore mentioned memory, for extracting partial sequences having a prescribed base length from the aforementioned nucleotide sequences based on data on the aforementioned read plurality of DNA nucleotide sequences, for detecting certain conditions related to the positions of the aforementioned partial sequences and conditions of their absence in DNA nucleotide sequences other than the aforementioned DNA nucleotide sequences, for selecting partial sequences meeting the aforementioned conditions, and for determining the nucleotide sequences of primers capable of hybridizing specifically to the aforementioned plurality of DNA nucleotide sequences based on the aforementioned selected partial sequences;

(8) a method for designing primers, comprising the steps of: taking data on a plurality of DNA nucleotide sequences from a database including a plurality of different DNA nucleotide sequences; extracting partial sequences having a certain base length from the aforementioned plurality of DNA nucleotide sequences based on the aforementioned nucleotide sequence data obtained above; detecting certain conditions related to the positions of the aforementioned partial sequences, and conditions of their absence in DNA nucleotide sequences other than the aforementioned DNA nucleotide sequences; selecting partial sequences meeting the aforementioned conditions from the aforementioned partial sequences based on the aforementioned detecting results; and determining the nucleotide sequences of primers capable of specifically hybridizing to the aforementioned DNA nucleotide sequences based on the aforementioned selected partial sequences;

(9) a computer-readable storage medium used in bioinformatics, the aforementioned storage medium comprising recorded data on a plurality of primers capable of specifically hybridizing to mutually different DNAS, and genetic data on DNA fragments amplified by PCR using the aforementioned plurality of primers, which are correlated each other;

(10) a computer-readable storage medium comprising data on a plurality of primers capable of specifically hybridizing to mutually different DNAS, and genetic data on DNA fragments amplified by PCR using the aforementioned plurality of primers, which are correlated each other, as well as a recorded program for displaying on a display device genetic data on the aforementioned DNA fragments corresponding to data on the aforementioned plurality of primers input by means of input/output unit of a computer;

(11) a method for analyzing DNA, comprising the analysis of sample DNA using as an indicator the type of primer affording PCR amplified fragments among the aforementioned plurality of primers, using a DNA analysis kit comprising a storage medium according to (9) or (10) above and a plurality of primers, the data for which have been recorded on the aforementioned storage medium;

(12) a DNA analysis kit, comprising a storage medium according to (9) or (10) above, and a plurality of primers for which the aforementioned primer data are recorded;

(13) PCR plates, comprising 75 or more types of solution comprising 1 or more primers;

(14) micro-well plates for PCR, comprising a plurality of solutions comprising 1 or more primers, the primer concentration in the aforementioned solutions ranging between 10 and 100 pmol/$\mu$L, with no enzymes that degrade the primers in the aforementioned solutions;

(15) micro-well plates for PCR, comprising a plurality of wells, 80% or more of the total of the aforementioned plurality of wells containing mutually different solutions comprising 1 or more primers;

(16) micro-well plates for PCR according to out of from (13) to (15) above, comprising the plurality of primers designed by means of a primer design method comprising the steps of: taking data on a plurality of DNA nucleotide sequences from a database including a plurality of different DNA nucleotide sequences; limiting the base length of the aforementioned plurality of DNA nucleotide sequences to a certain base length based on the aforementioned nucleotide sequence data taken above; extracting first partial sequences having a certain base length from the aforementioned limited nucleotide sequences; selecting second partial sequences meeting selection conditions related to GC content and/or Tm from the aforementioned first partial sequences; detecting certain conditions related to the positions of the aforementioned second partial sequences, and conditions of their absence in DNA nucleotide sequences other than the aforementioned DNA nucleotide sequences; selecting third partial sequences meeting the aforementioned conditions from the aforementioned second partial sequences based on the aforementioned detected results; and determining the nucleotide sequence of primers capable of specifically hybridizing to the aforementioned DNA nucleotide sequences based on the aforementioned third partial sequences;

(17) micro-well plates for PCR according to out of from (13) to (15) above, comprising a plurality of primers designed by means of a primer design method comprising the steps of: taking data on a plurality of DNA nucleotide sequences from a database including a plurality of different DNA nucleotide sequences; selecting DNA nucleotide sequences meeting selection conditions related to GC content and/or Tm from a plurality of DNA nucleotide sequences, the data for which have been obtained above; extracting partial sequences having a certain base length from the aforementioned selected nucleotide sequences; detecting certain conditions related to the positions of the aforementioned partial sequences, and conditions of their absence in DNA nucleotide sequences other than the aforementioned DNA nucleotide sequences; selecting partial sequences meeting certain conditions from the aforementioned partial sequences based on the aforementioned detected results; and determining the nucleotide sequence of primers capable of specifically hybridizing to the aforementioned DNA nucleotide sequences based on the aforementioned selected partial sequences;

(18) a PCR amplifying kit comprising a plurality of primers and a computer-readable storage medium, the aforementioned PCR amplifying kit comprising containers containing the aforementioned plurality of primers, ID codes assigned to the primers contained in the containers being indicated on the aforementioned containers, and a table correllating the aforementioned ID codes of the aforementioned plurality of primers with either the name, molecular formula, or sequence data for the aforementioned plurality of primers being recorded on the aforementioned storage medium.

DESCRIPTION OF THE PREFERRED EMBODIMENTS

The present invention is described in detail below.

Figure 2:
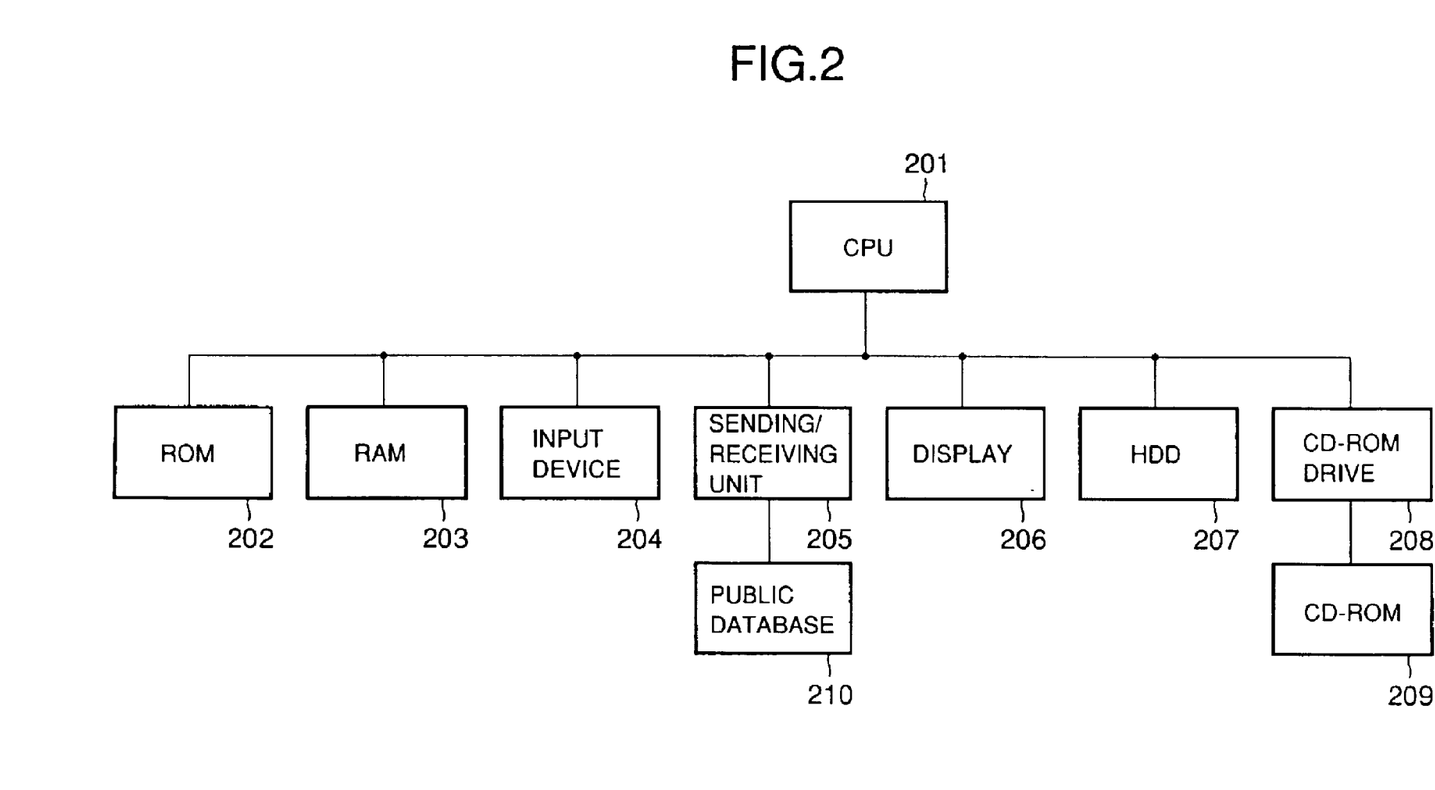
FIG. 2 is a block diagram illustrating an example of the structure of the primer design system in the present invention.

FIG. 2 is a block diagram illustrating an example of the structure of the primer design system in the present invention. The primer design system illustrated in FIG. 2 comprises CPU 201, ROM 202, RAM 203, input 204, transmitter/receiver 205, display 206, hard disc drive (HDD) 207, and CD-ROM drive 208. A re-writable CD-R or CD-RW can be used as storage medium instead of the CD-ROM 209. In such cases, CD-R or CD-RW drive is used instead of the CD-ROM drive 208. DVD, ZiP, MO, PD and corresponding drives for such media may also be used as the media for storing the large volume of primer-related data instead of the CD-ROM 209.

The CPU 201 runs the primer designing process described below and controls the primer design system as a whole according to programs stored on the ROM 202, RAM 203, or hard disc drive (HDD) 207. ROM 202 stores the programs or the like giving commands for the process needed to operate the primer design system. RAM 203 temporarily stores data necessary for running the primer design process. The input 204 is a keyboard, mouse, or the like, and is used to input the necessary conditions for running the primer design process. The transmitter/receiver 205 transfers data to and from public databases 210 or the like through communication lines based on commands from the CPU 201. The display 206 displays DNA nucleotide sequences obtained from databases, various conditions input from the input 204, designed primer nucleotide sequences, and the like based on commands from the CPU 201. The hard disc drive (HDD) 207 stores databases and the like comprising a plurality of different DNA nucleotide sequences and the primer design program, reads the stored programs, data, and the like based on commands from the CPU 201, and stores them in RAM 203, for example. The CD-ROM drive 208 reads programs, data, and the like from databases comprising a plurality of different DNA nucleotide sequences and the primer design program stored in the CD-ROM 209 based on commands from the CPU 201, and stores them in RAM 203, for example.

In the primer design system of the present invention, the receiver receives DNA nucleotide sequences from a database comprising a plurality of different DNA nucleotide sequences.

In the primer design system illustrated in FIG. 2, DNA nucleotide sequences contained in a public database 210 (a first database), for example, can be received by the transmitter/receiver 205 through communications lines, and these DNA nucleotide sequences can be stored in RAM 203.

Specific examples of a public database 210 include databases which can be used over the Internet (WWW (world wide web)). More specific examples include GenBank (nucleic acid nucleotide sequence (including DDBJ) database, prepared by NCBI (USA), National Genetic Research Institute), EMBL (nucleic acid nucleotide sequence database, prepared by EBI (Europe)), nr-nt (nucleic acid nucleotide sequence database, prepared from GenBank and EMBL), GENOME (KEGG genome maps, prepared by Kyoto University Chemical Research Institute), GENES (KEGG gene catalogs, prepared by Kyoto University Chemical Research Institute), CHR21 (sequence map for chromosome 21, prepared by HGC), JST (JST human genome sequencing database, prepared by Japan Science and Technology Corporation), BodyMap (human gene expression database, prepared by Osaka University), GENOTK (human cDNA database, prepared by Otsuka Pharmaceutical Co. Ltd., HGC), and MBGD (microorganism genome database, prepared by HGC). Nucleotide sequences received from a public database 210 may be either cDNA nucleotide sequences or genomic DNA nucleotide sequences, or partial sequences thereof. When the nucleotide sequences obtained from a public database 210 are cDNA nucleotide sequences, the cDNA nucleotide sequences received by the transmitter/receiver 205 are stored without modification in RAM 203. When the nucleotide sequences obtained from a public database 210 are genomic DNA nucleotide sequences, the genomic DNA nucleotide sequences are processed by an exon predicting program stored in ROM 202, hard disc drive (HDD) 207, or CD-ROM 209 which predicts the exon nucleotide sequences based on the genomic DNA nucleotide sequences, and the predicted exon nucleotide sequences are then stored in RAM 203. Existing exon predicting programs such as GENSCAN, GRAIL, and ER (Exon Recognizer) can be used as the exon predicting program.

In the primer design system illustrated in FIG. 2, DNA nucleotide sequences included in a database stored, for example, in the hard disc drive (HDD) 207 or CD-ROM 209 can be read based on commands from the CPU 201 and stored in RAM 203. A specific example of a database stored in the hard disc drive 207 or CD-ROM 209 is a locally built database using a public database.

Figure 3:
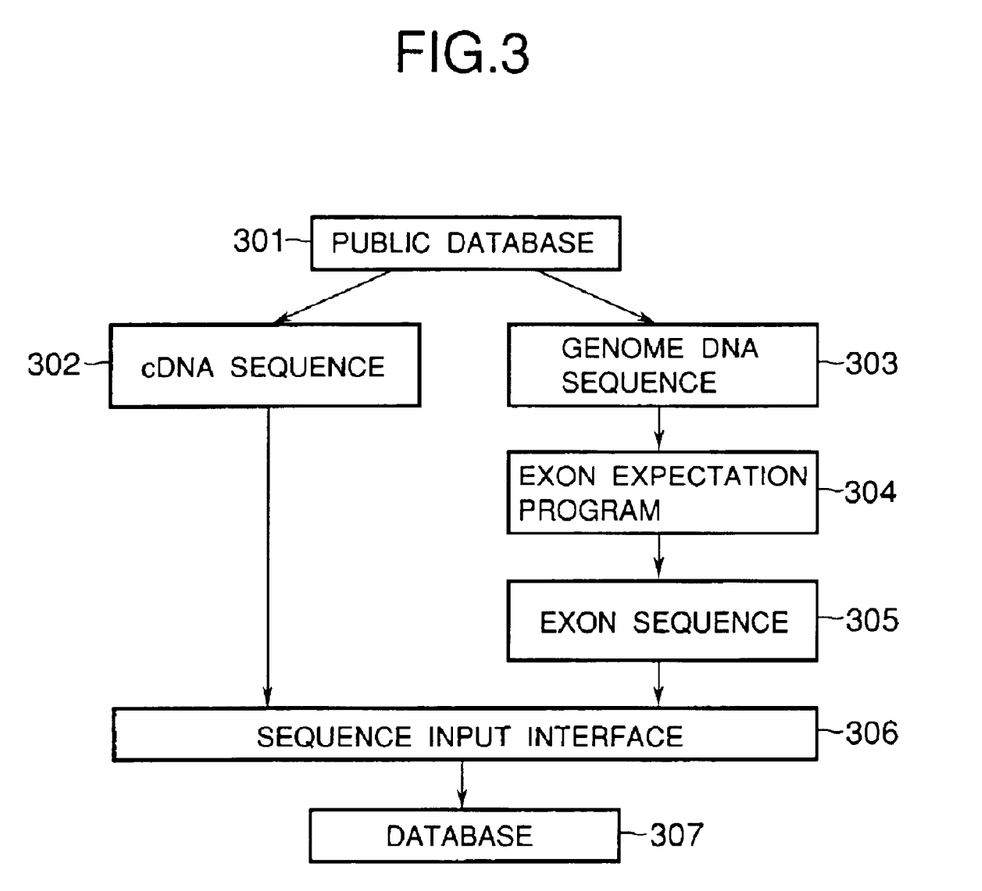
FIG. 3 is a flow chart illustrating the construction of a database using a public database.

FIG. 3 is a flow chart illustrating the construction of a database using a public database.

cDNA sequences 302 included in a public database 301 (a first database), and exon sequences 305 obtained when genomic DNA sequences 303 included in a public database 301 are processed by the exon predicting other recordable storage medium through a sequence input interface 306, so as to construct a database 307 (a second database). When constructing the database, the cDNA nucleotide sequences or exon nucleotide sequences can be divided to suitable lengths (such as 1 kb) and stored in a storage medium. Existing exon predicting programs such as GENSCAN, GRAIL, and ER (Exon Recognizer) can be used as the exon predicting program, and these programs can be used over the Internet. The database 307 built in this manner contains a plurality of different DNA nucleotide sequences.

The CPU 201 supplies the DNA nucleotide sequences received from the database to the display 206, and runs the process for designing primers capable of hybridizing specifically to the DNA received from the database (hereinafter referred to as "primer design process"). In the primer design system of the present invention, after the DNA nucleotide sequences have been received by the receiver, the primer design process is run by fragment length limiting process, partial sequence extracting process, partial sequence detecting process, partial sequence selecting process, and primer sequence determining process.

Figure 4:
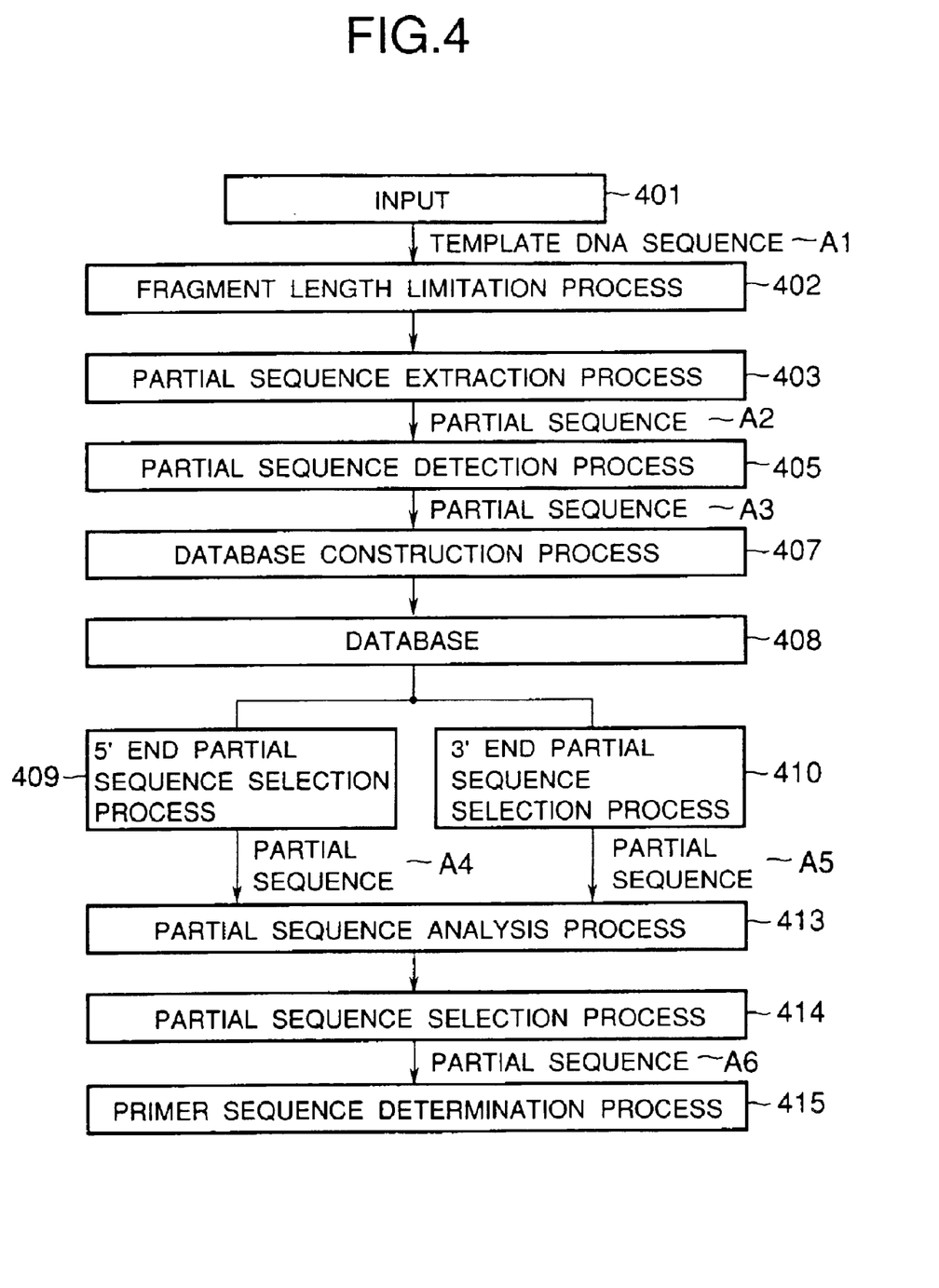
FIG. 4 is a block diagram illustrating an example of the structure of a primer designing program.

FIG. 4 is a block diagram illustrating an example of the structure of a primer designing program.

The CPU 201 supplies the DNA nucleotide sequences received from the database to the input 401 as nucleotide sequence informations of DNA serving as template (hereinafter referred to as "template DNA") for the primers to be designed. The input 401 supplies a template DNA sequence A1 to a fragment length limitation process 402. The fragment length limitation process 402 modifies the template DNA sequence A1 to a length suitable for amplification in which the designed primers will be used, and then supplies it to a partial sequence extraction process 403. A partial sequence of prescribed base length (such as 20 to 28 bases) is extracted from the template DNA sequence by the partial sequence extraction process 403, and the extracted partial sequence A2 (a first partial sequences) is supplied to the partial sequence detection process 405. The partial sequence detection process 405 determines whether or not the extracted partial sequence A2 meets certain detection conditions (such as GC content: the proportion between the sum of cytosine and guanine content and the sum of adenine and thymine content in double-stranded DNA molecules; or Tm: the temperature at which the double-stranded portion of DNA or RNA molecules is denatured into single strands, resulting in a double-stranded/single-stranded ratio of 1:1). The detection conditions can be selected as desired. Specific examples of such detection conditions include conditions under which the GC content is 50 to 60%, the Tm is between 50 and 80° C., and |Tm| is below 20° C. The partial sequence detection process 405 supplies the partial sequence A3 (a second partial sequences) meeting the prescribed detection conditions to a database constructing process 407 (a second selecting means). The partial sequence detection process 405 may also be provided after the input 401 in order to detect GC content, Tm, or the like for the template DNA sequence A1 supplied to the input 401, allowing partial sequences meeting certain fixed conditions to be supplied to the fragment length limitation process 402 (a third selecting means). The database construction process 407 constructs a database 408 comprising the partial sequence A3 meeting the prescribed detection conditions. From the partial sequences contained in the database 408, a 5' partial sequence selection process 409 selects partial sequences located closest to the 5' end among the partial sequences derived from the one template DNA sequence A1. From the partial sequences contained in the database 408, a 3' partial sequence selection process 410 selects partial sequences located closest to the 3' end among the partial sequences derived from one template DNA sequence A1. The partial sequences A4 selected by the 5' partial sequence selection process 409 and the partial sequence A5 selected by the 3' partial sequence selection process 410 are supplied to a partial sequence analysis process 413. The partial sequence analysis process 413 analyzes whether or not the supplied partial sequences A4 or A5 are present in a DNA nucleotide sequences other than the template DNA. To determine whether or not the supplied partial sequences are present in DNA nucleotide sequences other than the template DNA, the partial sequence analysis process 413 analyzes data compiled in public databases and the like by means of a homology screening program. BLAST or FASTA, for example, can be used as the homology screening program. A partial sequence selection process 414 selects partial sequences that are not present in DNA nucleotide sequences other than the template DNA and supplies the selected partial sequence A6 (a third partial sequences) to a primer determination process 415 (a first selecting means). The primer sequence determination process 415 determines the nucleotide sequence of primers based on the partial sequences that are supplied. For example, the primer sequence determination process 415 determines the nucleotide sequence that is complementary to the partial sequence of the 5' end that has been supplied as nucleotide sequence of forward primer, and also determines the nucleotide sequence that is complementary to the partial sequence of the 3' end that has been supplied as nucleotide sequence of reverse primer. Primers capable of hybridizing specifically to the template DNA can be designed in this manner.

Figure 5:
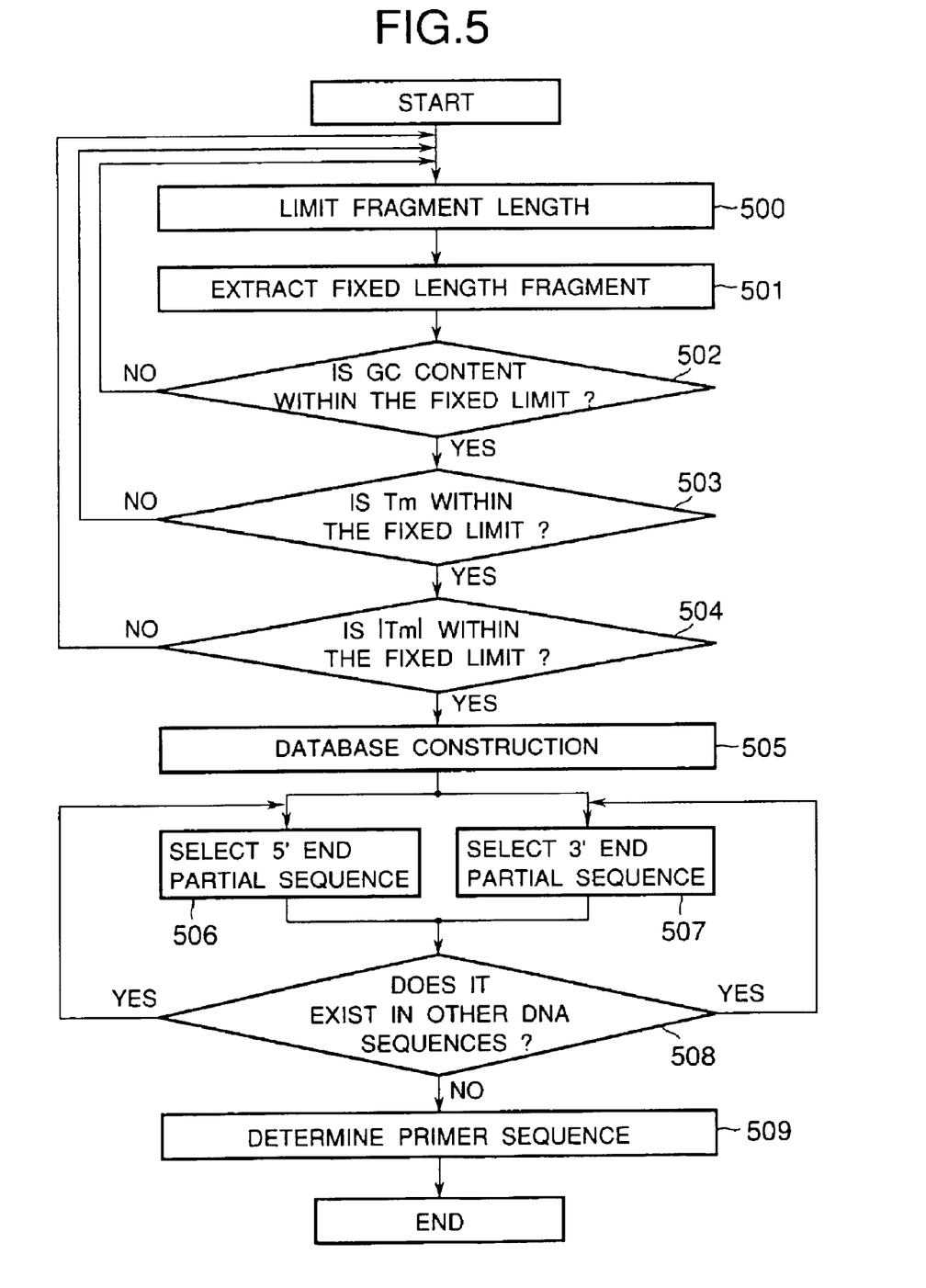
FIG. 5 is a flow chart illustrating an example of a process using the program illustrated in FIG. 4.

FIG. 5 is a flow chart illustrating an example of a process using the program illustrated in FIG. 4.

The nucleotide sequence serving as the template is first read from the database 307, and the program is started. A partial sequence A2 of prescribed base length (such as 20 to 28 bases) is extracted by the partial sequence extraction process 403 (step 501) from each template DNA sequence A1 modified by the fragment length limiter 402 to a length which can be amplified (step 500). The partial sequence detection process 405 determines whether or not the GC content of the extracted partial sequence A2 is within a prescribed range (such as 50 to 60%) (step 502). When the GC content of the extracted partial sequence A2 is not within the prescribed range (such as 50 to 60%), another partial sequence A2 is extracted by the partial sequence extraction process 403 (step 501). When the GC content of the extracted partial sequence A2 is within the prescribed range (such as 50 to 60%), it is then determined whether or not the Tm is within a prescribed range (such as 50 to 80° C.) (step 503). When the Tm of the extracted partial sequence A2 is not within the prescribed range (such as 50 to 80° C.), another partial sequence A2 is extracted by the partial sequence extraction process 403 (step 501). When the Tm is within the prescribed range (such as 50 to 80° C.), it is then determined whether or not |Tm| is within a prescribed range (such as below 20° C.) (step 504). When the |Tm| of the extracted partial sequence A2 is not within the prescribed range (such as below 20° C.), another partial sequence A2 is extracted by the partial sequence extraction process 403 (step 501). When the |Tm| is within the prescribed range (such as below 20° C.), the partial sequence is recorded in a re-writable storage medium such as the hard disc or CD-R by the database construction process 407 (step 505). Steps 501 through 505 are repeated for all partial sequences that can be extracted from the template DNA sequence to construct a database of partial sequences A3 meeting the prescribed extraction conditions (such as a base length of 20 to 28 bases, a GC content of between 50 and 60%, a Tm of between 50 and 80° C., and a |Tm| of below 20° C.) (step 505 (a second selecting means)). From the partial sequences contained in the database that has been constructed, the 5' partial sequence selection process 409 selects partial sequences located closest to the 5' end (step 506). In addition, from the partial sequences contained in the database that has been constructed, the 3' partial sequence selection process 410 selects partial sequences located closest to the 3' end (step 507). The partial sequence A4 selected by the 5' partial sequence selection process 409 and the partial sequence A5 selected by the 3' partial sequence selection process 410 are analyzed by the partial sequence analysis process 413 to determine whether or not they are present in DNA nucleotide sequences other than the template DNA (step 508). When the partial sequence A4 selected by the 5' partial sequence selection process 409 is present in a DNA nucleotide sequence other than the template DNA, the partial sequence located second closest to the 5' end is then selected from the partial sequences contained in the database that has been constructed (step 506). When the partial sequence A5 selected by the 3' partial sequence selection process 410 is present in a DNA nucleotide sequence other than the template DNA, the partial sequence located second closest to the 3' end is then selected from the partial sequences contained in the database that has been built (step 507). Steps 506 through 508 are repeated until a partial sequence that is not present in a DNA nucleotide sequence other than the template DNA is selected (a first selecting means). Partial sequences that are not present in DNA nucleotide sequences other than the template DNA are selected by the partial sequence selection process 414, and the selected partial sequences A6 are supplied to the primer sequence determination process 415. Primers capable of hybridizing specifically to the template DNA are designed by the primer sequence determination process 415 based on partial sequences that are not present in DNA nucleotide sequences other than the template DNA (step 509).

The primers designed by means of the primer design system of the present invention can be chemically synthesized by a common method according to their nucleotide sequences. The primer design system of the present invention makes it possible to efficiently design a plurality of primers capable of hybridizing to mutually different DNAs.

In the present embodiment, partial sequences closest to the 5' or 3' end were selected after detection of Tm or the like, and sequences analyzed as not being included anywhere except in the template DNA were determined as primer sequences, but the order of the detection, selection, and analysis may be changed. When exons in their entirety are to be analyzed, or when exon-intron junctions are to be analyzed, the object of primer design is not limited to exon regions, and the partial sequences for introns can also be used for template DNAs. A plurality of primers capable of specifically hybridizing to mutually different DNAs can be used in DNA analysis. For example, sample DNA can be used as template, PCR can be run using a plurality of primers capable of specifically hybridizing to mutually different DNAs, and the sample DNA can be analyzed using as markers the types of primers giving the PCR amplified fragments. For example, during the analysis of differences in gene levels between normal individuals and patients afflicted with a certain disease (such as cancer), genomic DNA extracted from the cells of individuals can be used as templates, PCR can be run using a plurality of primers capable of hybridizing specifically to mutually different DNAs, and DNA regions (such as exons) potentially related to the disease can be determined based on types of primers having differences in nucleotide sequence and the length or presence/absence of amplified fragments between normal individuals and patients. High-throughput screening is made possible by DNA analysis thus using a plurality of primers capable of hybridizing specifically to mutually different DNAs.

In DNA analysis featuring the use of a plurality of primers capable of hybridizing specifically to mutually different DNAs, it is important to collate the data of the primers with the genetic data of the DNA fragments amplified by PCR using the primers. Specifically, it is important to determine the genetic data of the DNA fragments amplified using the primers based on the data of the primers affording the fragments amplified by PCR. It is thus desirable to use a computer-readable storage medium in which are recorded the data of the plurality of primers capable of hybridizing specifically to mutually different DNAS, and the genetic data of the DNA fragments amplified by PCR using these primers. A program for allowing the display of the genetic data of the DNA fragments amplified by PCR using these primers based on the data of the primers input to a computer may be recorded in the storage medium. The program may also be recorded in another storage medium.

The primer data include primer nucleotide sequences, data characterizing the primer (such as identifying name), or the like. The genetic data of the DNA fragments include DNA fragment nucleotide sequences, data related to the function of the proteins encoded by the DNA fragments (whether or not functions have been elucidated, and which functions have been elucidated), or the like. Storage media include CD-ROM, hard disc, ROM, RAM, DVD, and CD-R/RW.

The aforementioned DNA analysis can be performed using a DNA analysis kit comprising a plurality of primers capable of hybridizing specifically to mutually different DNAs, and the aforementioned storage medium. A PCR amplifying kit comprising a plurality of primers and a computer-readable storage medium can be used in the aforementioned DNA analysis. Each of the aforementioned plurality of primers is contained in a plurality of containers in such a PCR amplifying kit, ID codes given to the primers contained in the containers are indicated on the aforementioned plurality of containers, and a table collating the ID codes of the aforementioned plurality of primers with either the name, molecular formula, or sequence data for the aforementioned plurality of primers is recorded in the aforementioned storage medium. Plates having a plurality of wells as described below can be used as the containers.

DNA can be analyzed using the aforementioned DNA analysis kit in the following manner, for example. An identification name (ID code) such as B1, B2, B3 through Z7, Z8, Z9, for example, is given to each primer as data characterizing the primers, and "B5" is input as primer data to the input 204 when the primer giving PCR amplified fragments is B5 during PCR run with the primers. The CPU 201 determines the genetic data of the DNA fragments which have been amplified by PCR using primer B5 based on the input primer data in accordance with the program stored in ROM 202, RAM 203, hard disc 207, or CD-ROM 209, and displays on the display 206.

For efficient analysis of large amounts of sample DNA during DNA analysis, it is possible to use plates having a plurality of wells, which are plates containing in some of the wells solutions containing the plurality of primers capable of hybridizing specifically to mutually different DNAs. Such plates can be used to carry out PCR all at once using a plurality of primers for sample DNAs, thus allowing the sample DNAs to be efficiently analyzed and large amounts of sample DNA to be analyzed. PCR featuring the use of such plates can be carried out with commercially available automated devices such as automatic reaction robots.

The number of plate wells and the number and type of primers contained in the plates are not particularly limited. Plates may have wells which do not contain solutions with primers, or all the wells may contains solutions containing primers. Each well may contain solutions with one type of primer, or solutions with 2 or more types of primers. Although different wells usually contains solutions with different types of primers, different wells may also contain solutions with the same types of primers.

For comprehensive DNA analysis, 75 or more types of solutions in all should be contained per plate. For even higher analyzing efficiency, 80% or more of the total number of wells should contain different solutions.

Commercially available 96-well plates, 384-well plates, and the like can be used as the plates with a plurality of wells. In such cases, PCR can be carried out for large amounts of sample DNAs with each plate having 76 or 307 kinds of solutions with primers.

The composition of the solutions containing the primers is not particularly limited, provided that PCR can be carried out in the solutions. Since the PCR reaction solution usually contains $H_2O$, PCR buffer, $MgCl_2$, dNTP mix, Taq polymerase, and the like in addition to primers and template DNA, the solutions containing the primers may contain 1 or more thereof.

The primer concentration in the solution can be selected as desired, but is preferably between 10 and 100 pmol/$\mu$L. Conventionally, the concentration is a thick one on the order of micromol/mL, and is diluted for use, but when the concentration is about 10 to 100 pmol/$\mu$L from the beginning, the user can use it immediately. The solution should also contain no enzymes that degrade the primers (such as DNase).

The plates may also comprise lids, films or the like to cover the wells so as to prevent the primer solutions in the wells from becoming mixed with each other during distribution. When the film is one that can be broken by a robot liquid handling capillary, an advantage is that it can be mounted on the robot as is.

Embodiment 1

A relatively new sequence which had not been analyzed very much was selected from the sequence database for chromosome 21 publicly disclosed on the World-wide Web (ER1 Chromosome 21 Sequence Database) Processing this sequence by existing exon predicting programs (programs A and B) resulted in the prediction of four sequences (exon 1: SEQ ID NO: 1; exon 2: SEQ ID NO: 2; exon 3: SEQ ID NO: 3; exon 4: SEQ ID NO: 4) as exon nucleotide sequences. The machine used to predict the exons was a SUN Ultra 60 (2 GB memory), and the prediction time was about 5 minutes per sequence with program A (mail server) and about 10 minutes with program B (local server).

Partial sequences meeting the following extraction conditions were extracted from each of the predicted exon nucleotide sequences:

(1) base length: 20 to 28 bps;

(2) GC content: 50 to 60%;

(3) Tm: 50 to 80° C.; |Tm|: below 20° C.; and (4) located as close as possible to the 5' end or 3' end.

A Blast search was performed on the GenBank database with the extracted partial sequences as the query, and an Identities value of 50% or lower was selected to screen for partial sequences of high specificity. When screening of partial sequences of even higher specificity is desired, the Identities value can be set lower (such as 30% or lower), and when other conditions are to be prioritized at the expense of a certain degree of specificity, a higher value (such as 70% or more) can be set.

Figure 6:
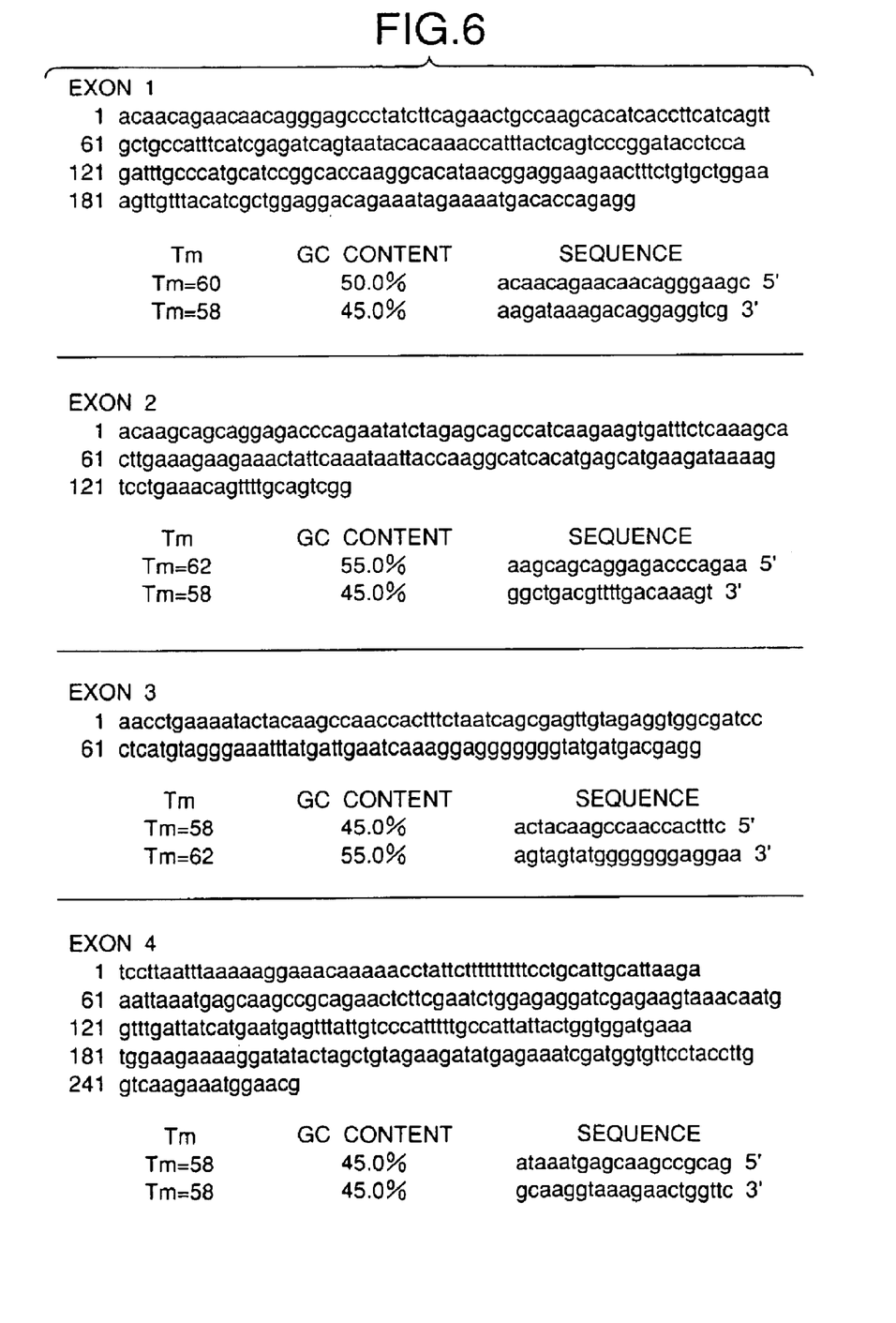
FIG. 6 illustrates exon sequences selected from the sequence database 21, and partial sequences extracted from those exon sequences specific extraction conditions; specifically, exon 1 (SEQ ID NO: 1) and its extracted partial sequences (SEQ ID NO: and 6), exon 2 (SEQ ID NO: 2) and its extracted partial sequences (SEQ ID NO: 7 and 8), exon 3 (SEQ. ID NO: 3) and its extracted partial sequences (SEQ ID NO: 9 and 10), and exon 4 (SEQ ID NO: 4) and its extracted partial sequences (SEQ ID NO: 11 and 12)

As a result, the partial sequences given in SEQ ID NOS:5 and 6 were extracted from exon 1 (SEQ ID NO:1), the partial sequences given in SEQ ID NOS:7 and 8 were extracted from exon 2 (SEQ ID NO:2), the partial sequences given in SEQ ID NOS:9 and 10 were extracted from exon 3 (SEQ ID NO:3), and the partial sequences given in SEQ ID NOS:11 and 12 were extracted from exon 4 (SEQ ID NO:4) (FIG. 6).

Embodiment 2

The time needed to execute the following patterns I through III one thousand times was calculated. A SUN Ultra 60 (2 GB memory) computer capable of locally running the necessary programs was used for each of the patterns.

Pattern I

Only primer designing was carried out. Pattern I involved running a process for designing a pair of partial sequences from the predetermined template DNA sequence A1, which is preferably predicted and screened, based on primer design software corresponding to the partial sequence designing processors 403–415 in FIG. 4. The partial sequence designing conditions were as follows.

(1) base length: 20 to 28 bps;
(2) GC content: 50 to 60%:
(3) Tm: 50 to 80° C.; |TM|: below 20° C.; and
(4) located as close as possible to the 5' end or 3' end.

Pattern II

For pattern II, exons were screened, and primers were then designed. For pattern II, exons were screened based on selected conditions from previously prepared exon database 307, then the template DNA sequence A1 (i.e., a screened exon) was transferred through the input 4-1 to the partial sequence designing processors 403–415 in FIG. 4 such that the process for designing partial sequences was run based on primer design software. The exon screening conditions are given below. The partial sequence designing conditions were the same as for pattern I.

(1) exon length: 300 bps or less
(2) exons predicted by an exon predicting program
(3) found in EST database, and expression confirmed
(4) unknown function (not found in protein database)
(5) SNP potential (variation in EST database)

Pattern III

After the exon prediction, exons were screened, and primers were then designed. For pattern III, exons were predicted using software corresponding to the exon predicting program 304 from genomic DNA sequences 303, the output exon sequences 305 were compiled into a database 307 through a sequence input interface 306, exons were screened in the exon database 307 on the basis of the set conditions, then the template DNA sequence A1 (i.e., a predicted then screened exon) was transferred through the input 401 to the partial sequence designing processors 403–415 in FIG. 4 such that the process for designing partial sequences was run by primer design software. The exon screening conditions were the same as for pattern II. The partial sequence extraction conditions were the same as for pattern 1.

Table 1 shows the results of calculations for the time needed to run patterns I through III one thousand times, respectively. In Table 1, "T1" represents that time (minutes) needed for exon prediction, "T2" represents the time (minutes) needed for exon screening, and "T3" represents the time (minutes) needed for primer design.

TABLE 1

|  | I | II | III |
|---|---|---|---|
| T1 (min) | 0 | 0 | 1244.8 |
| T2 (min) | 0 | 598.2 | 598.2 |
| T3 (min) | 49.8 | 49.8 | 49.8 |
| Calculated time (min) needed to design 1000 primers | 49.8 | 648 (10.8 H) | 1892.8 (31.55 H) |
| When simultaneously treated by parallel processes (here, 50) by parallel and distributed computers | 1.0 | 13.0 | 37.9 |

The results of Table 1 show that the primer design system of the present invention can be used to design about 5000 sets of primers per day through parallel and distributed computers, which means about 150,000 primers could be sufficiently prepared a year.

The primer design system of the present invention allows a plurality of primers capable of hybridizing specifically to mutually different DNAs to be efficiently prepared. The plurality of primers capable of hybridizing specifically to mutually different DNAS can be used in DNA analysis, allowing large amounts of sample DNAs to be efficiently analyzed all at once. It is particularly useful for high throughput screening. During DNA analysis, a computer-readable storage medium in which are recorded data for the plurality of primers capable of hybridizing specifically to mutually different DNAs and genetic data for DNA fragments amplified by PCR using these primers can be used to make such DNA analysis easier.

All publications, patents and patent applications cited herein are incorporated herein by reference in their entirety.

What is claimed is:

1. A primer design system, comprising:
   means for selecting at least one genomic DNA nucleotide sequence from a database including a plurality of genomic DNA nucleotide sequences;
   means for predicting a plurality of exons of said selected DNA nucleotide and for storing positions of the predicted exons;
   means for designing a plurality of primer pairs for each of the simultaneously by using each of the predicted exons as a template to design one corresponding primer pair for each of the predicted exons; and
   means for automatically collating said plurality of primer pairs with said predicted exons and the DNA nucleotide sequence.

2. The primer design system according to claim 1, further comprising means for selecting a plurality of primer pairs from the designed primer pairs meeting certain selection conditions.

3. The primer design system according to claim 2, wherein said selection conditions include at least one of a predetermined base length, a range of GC content and a range of melting temperature Tm.

4. The primer design system according to claim 1, further comprising means for evaluating specificity of each primer of a designed primer pair by a sequence alignment program.

5. The primer design system according to claim 1, further comprising means for randomly dividing fragments of a genomic DNA into templates for exon prediction.

6. A method for designing primers, comprising the steps of:
   selecting at least one genomic DNA nucleotide sequence from a genomic DNA database;
   predicting a plurality of exons of said selected DNA nucleotide;
   designing corresponding primer pairs for the predicted exons simultaneously by using each of the predicted exons as a template to design one corresponding primer pair for each of the predicted exons; and
   automatically collating said plurality of primer pairs with said predicted exons and the DNA nucleotide sequence.

7. The method for designing primers according to claim 6, further comprising a step of selecting a plurality of primer pairs meeting certain selection conditions from said plurality of designed primer pairs, wherein said selection conditions include at least one of a predetermined base length, a GC content and a range of melting temperature Tm.

8. The method for designing primers according to claim 6, further comprising a step of evaluating specificity of each primer of a designed primer pair.

9. A primer design system, comprising:

means for selecting at least one genomic DNA nucleotide sequence from a database including a plurality of genomic DNA nucleotide sequences;

means for predicting a plurality of exons of said selected DNA nucleotide and for storing positions of the predicted exons;

means for designing a plurality of primer pairs simultaneously by using each of the predicted exons as a template to design one corresponding primer pair for each of the predicted exons; and means for evaluating specificity of each primer of designed primer pairs.

10. The primer design system according to claim 9, wherein the system is capable of evaluating each designed primer by conducting homology searches with a certain degree of specificity for a full sequence of the primer via at least one repeat database and at least one genome database.

* * * * *

SEQUENCE LISTING

<160> NUMBER OF SEQ ID NOS: 12

<210> SEQ ID NO 1
<211> LENGTH: 227
<212> TYPE: DNA
<213> ORGANISM: Homo sapiens

<400> SEQUENCE: 1
acaacagaac aacagggagc cctatcttca gaactgccaa gcacatcacc ttcatcagtt      60
gctgccattt catcgagatc agtaatacac aaaccattta ctcagtcccg gatacctcca     120
gatttgccca tgcatccggc accaaggcac ataacggagg aagaactttc tgtgctggaa     180

```
agttgtttac atcgctggag gacagaaata gaaaatgaca ccagagg              227
```

<210> SEQ ID NO 2
<211> LENGTH: 143
<212> TYPE: DNA
<213> ORGANISM: Homo sapiens

<400> SEQUENCE: 2

```
acaagcagca ggagacccag aatatctaga gcagccatca agaagtgatt tctcaaagca    60
cttgaaagaa gaaactattc aaataattac caaggcatca catgagcatg aagataaaag   120
tcctgaaaca gttttgcagt cgg                                          143
```

<210> SEQ ID NO 3
<211> LENGTH: 114
<212> TYPE: DNA
<213> ORGANISM: Homo sapiens

<400> SEQUENCE: 3

```
aacctgaaaa tactacaagc caaccacttt ctaatcagcg agttgtagag gtggcgatcc    60
ctcatgtagg gaaatttatg attgaatcaa aggagggggg gtatgatgac gagg         114
```

<210> SEQ ID NO 4
<211> LENGTH: 256
<212> TYPE: DNA
<213> ORGANISM: Homo sapiens

<400> SEQUENCE: 4

```
tccttaattt aaaaaggaaa caaaaaccta ttcttttttt tttcctgcat tgcattaaga    60
aattaaatga gcaagccgca gaactcttcg aatctggaga ggatcgagaa gtaaacaatg   120
gtttgattat catgaatgag tttattgtcc cattttgcc attattactg gtggatgaaa    180
tggaagaaaa ggatatacta gctgtagaag atatgagaaa tcgatggtgt tcctaccttg   240
gtcaagaaat ggaacg                                                  256
```

<210> SEQ ID NO 5
<211> LENGTH: 20
<212> TYPE: DNA
<213> ORGANISM: Homo sapiens

<400> SEQUENCE: 5

```
acaacagaac aacagggagc                                               20
```

<210> SEQ ID NO 6
<211> LENGTH: 20
<212> TYPE: DNA
<213> ORGANISM: Homo sapiens

<400> SEQUENCE: 6

```
aagataaaga caggaggtcg                                               20
```

<210> SEQ ID NO 7
<211> LENGTH: 20
<212> TYPE: DNA
<213> ORGANISM: Homo sapiens

<400> SEQUENCE: 7

```
aagcagcagg agacccagaa                                               20
```

<210> SEQ ID NO 8
<211> LENGTH: 20

-continued

```
<212> TYPE: DNA
<213> ORGANISM: Homo sapiens

<400> SEQUENCE: 8
ggctgacgtt ttgacaaagt                                              20

<210> SEQ ID NO 9
<211> LENGTH: 20
<212> TYPE: DNA
<213> ORGANISM: Homo sapiens

<400> SEQUENCE: 9
actacaagcc aaccactttc                                              20

<210> SEQ ID NO 10
<211> LENGTH: 20
<212> TYPE: DNA
<213> ORGANISM: Homo sapiens

<400> SEQUENCE: 10
agtagtatgg gggggaggaa                                              20

<210> SEQ ID NO 11
<211> LENGTH: 20
<212> TYPE: DNA
<213> ORGANISM: Homo sapiens

<400> SEQUENCE: 11
attaaatgag caagccgcag                                              20

<210> SEQ ID NO 12
<211> LENGTH: 20
<212> TYPE: DNA
<213> ORGANISM: Homo sapiens

<400> SEQUENCE: 12
gcaaggtaaa gaactggttc                                              20
```